US00PP29992P2

(12) United States Plant Patent
van Nijnatten

(10) Patent No.: US PP29,992 P2
(45) Date of Patent: Dec. 18, 2018

(54) JAPANESE HOLLY PLANT NAMED 'ANNYS5'

(50) Latin Name: *Ilex crenata*
Varietal Denomination: Annys5

(71) Applicant: Andre van Nijnatten, Zundert (NL)

(72) Inventor: Andre van Nijnatten, Zundert (NL)

( * ) Notice: Subject to any disclaimer, the term of this patent is extended or adjusted under 35 U.S.C. 154(b) by 0 days.

(21) Appl. No.: 15/530,720

(22) Filed: Feb. 21, 2017

(51) Int. Cl.
*A01H 5/00* (2018.01)

(52) U.S. Cl.
USPC ..... Plt./247

(58) Field of Classification Search
USPC ..... Plt./247

CPC ... A01H 5/12; A01H 5/00; A01H 5/02; A01H 5/08; A01H 6/00
See application file for complete search history.

(56) References Cited

PUBLICATIONS

Screen capture from YouTube video clip entitled "Plantipp presents *Ilex crenata* Luxus Globe" 5 pp. published Sep. 4, 2016. Retrieved from the Internet at https://www.youtube.com/watch?v=Kqn35tiHsRM. (Year: 2016).*

* cited by examiner

*Primary Examiner* — June Hwu
(74) *Attorney, Agent, or Firm* — Penny J. Aguirre

(57) ABSTRACT

A new cultivar of *Ilex crenata* plant named 'Annys5' that is characterized by its male flowers and therefore lacks berry formation, its compact and semi-upright plant habit, and its glossy leaves that are oblanceolate in shape and flat in aspect.

2 Drawing Sheets

Botanical classification: *Ilex crenata.*
Variety denomination: 'Annys5'.

CROSS REFERENCE TO A RELATED APPLICATION

This application is related to a European plant breeders' rights application filed on Mar. 27, 2013, Application No. 2013/0941. There have been no offers for sale anywhere in the world prior to the filing of this Application and no accessibility to one of ordinary skill in the art could have been derived from the printed plant breeder's rights documents.

BACKGROUND OF THE INVENTION

The present invention relates to a new and distinct cultivar of *Ilex crenata* and will be referred to hereafter by its cultivar name, 'Annys5'. 'Annys5' is a new cultivar of Japanese holly grown for use as a landscape plant.

The new *Ilex* resulted from a breeding program conducted by the Inventor in Zundert, The Netherlands. The Inventor made crosses between unnamed and unpatented proprietary plants of *Ilex crenata* in the Inventor's breeding program as both the female parent and male parent. The exact characteristics of the parents are unknown as seeds where pooled and sown from numerous crosses over different years. 'Annys5' was selected as a single unique plant in 2003 from the resulting seedlings of the above crosses.

Asexual reproduction of the new cultivar was first accomplished by the Inventor using semi-hardwood stem cuttings in 2003 in Zundert, The Netherlands. Asexual propagation by semi-hardwood stem cuttings has determined that the characteristics of the new cultivar are stable and are reproduced true to type in successive generations.

SUMMARY OF THE INVENTION

The following traits have been observed repeatedly and represent the characteristics of the new cultivar. These attributes in combination distinguish 'Annys5' as a unique cultivar of *Ilex*.

1. 'Annys5' exhibits male flowers and therefore berries are not formed.
2. 'Annys5' exhibits a compact and semi-upright plant habit.
3. 'Annys5' exhibits glossy leaves that are oblanceolate in shape and flat in aspect.

'Annys5' can be most closely compared to the *Ilex crenata* cultivar 'Beehive' (not patented) and 'Carolina Upright' (not patented). 'Beehive' is similar to 'Annys5' in having male flowers and glossy foliage. 'Beehive' differs from 'Annys5' in having a more spreading plant habit and leaves that are smaller and elliptic in shape. 'Carolina Upright' differs from from 'Annys5' leaves that broader, less glossy and convex in aspect, and in having female flowers.

BRIEF DESCRIPTION OF THE DRAWINGS

The accompanying colored photographs illustrate the overall appearance and distinct characteristics of a two-year-old plant of the new cultivar as grown outdoors in a 17-cm circular container in Zundert, The Netherlands.

photograph in FIG. 1 illustrates the plant habit of 'Annys5'.

Figure 1:
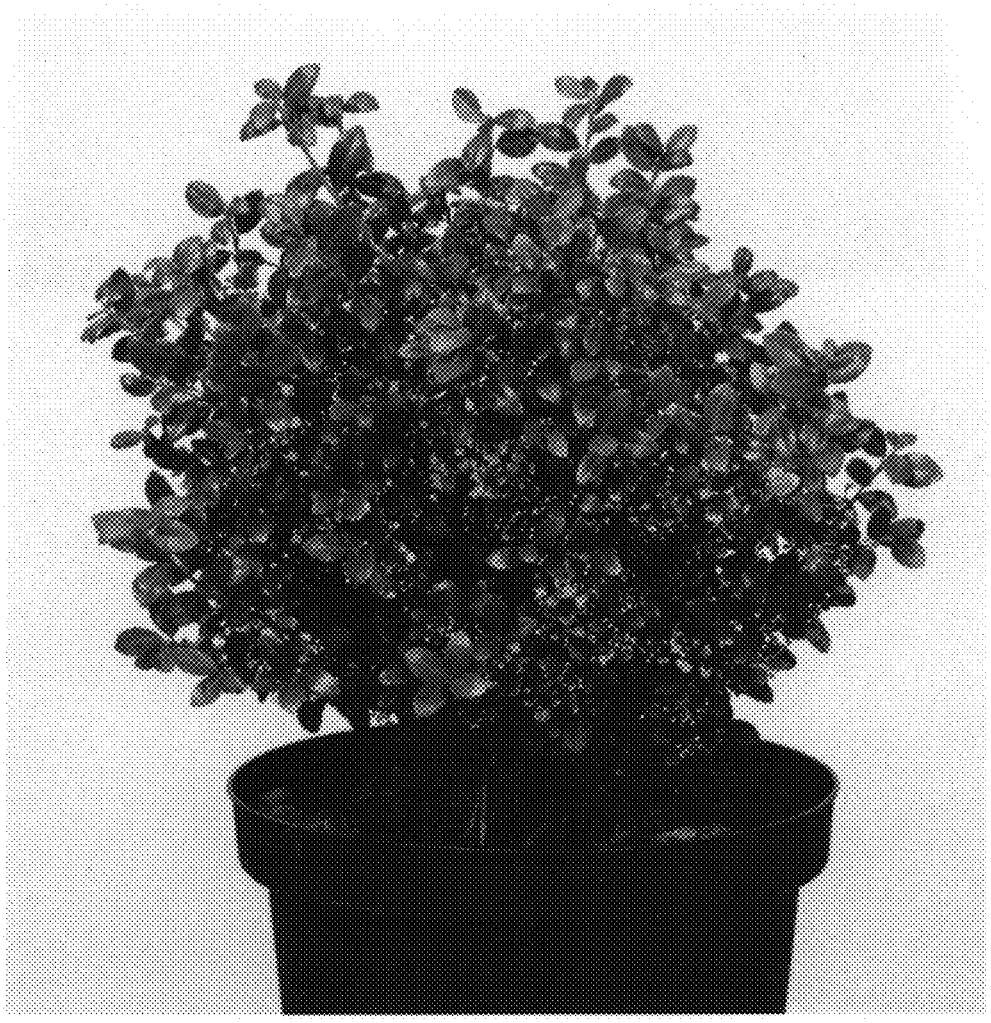
Figure 2:
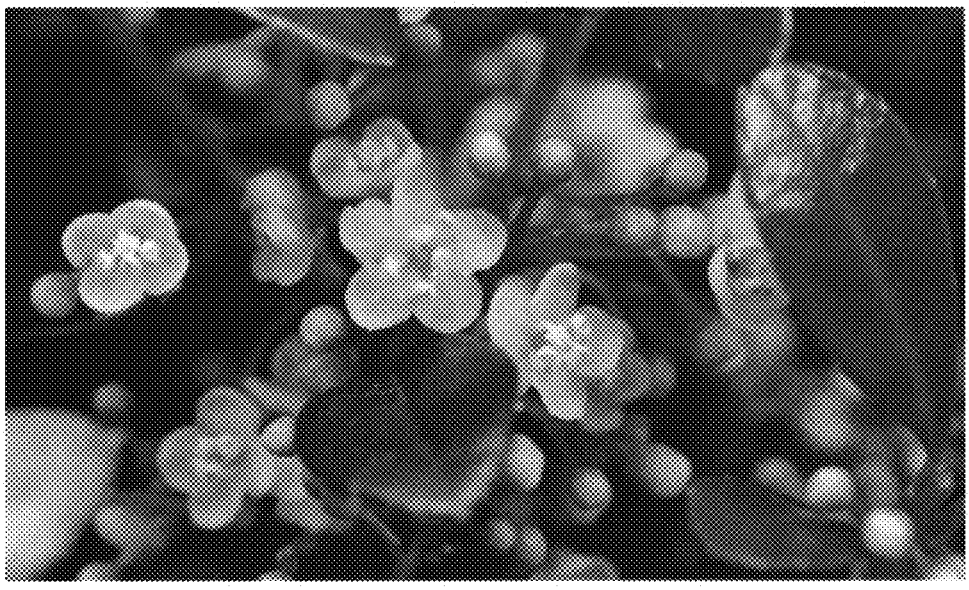

The photograph in FIG. 2 provides a close-up view of the flowers of 'Annys5'.

Figure 3:
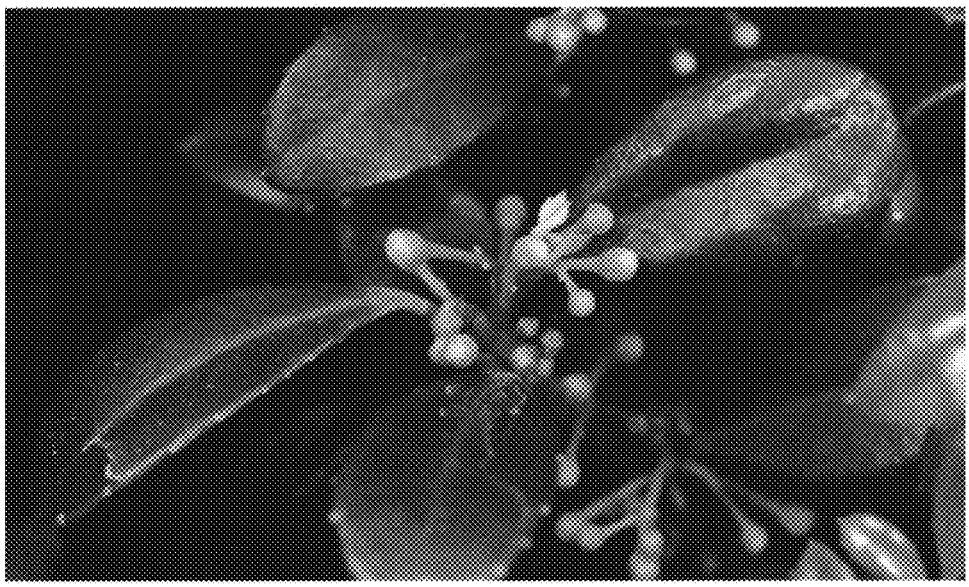

The photograph in FIG. 3 provides a close-up view of the foliage of 'Annys5'.

The colors in the photographs may differ slightly from the color values cited in the detailed botanical description, which accurately describe the colors of the new *Ilex*.

DETAILED BOTANICAL DESCRIPTION

The following is a detailed description of two-year-old plants of the new cultivar as grown outdoors in a 17-cm circular container in Zundert, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Plant type.*—Evergreen, perennial shrub.

*Plant habit.*—Compact and semi upright.

*Height and spread.*—Reaches 24 cm in height and 28 cm in diameter.

*Cold hardiness.*—At least to U.S.D.A Zones 6 to 10.

*Diseases.*—No susceptibility or resistance to diseases have been observed.

*Root description.*—Densly fibrous.

*Propagation.*—Semi-hardwood stem cuttings.

*Root development.*—An average of 10 weeks to fully root a liner and about one year to fully develop in a one-gallon container from a liner.

*Growth rate.*—Slow to moderate.

Stem description:

*Branching.*—Freely branching; 6 main branches, 35 lateral branches.

*Stem shape.*—Round.

*Stem strength.*—Strong.

*Stem size.*—Main stems; 1 cm in diameter, 3 cm in length, lateral branches; 2 mm in diameter, 13.4 cm in length.

*Stem surface.*—Young; slightly glossy, mature; slightly glossy, older stems; covered with smooth bark.

*Stem color.*—Young; 143B, mature; 137B, older stems; color between 197C and 199D.

*Stem aspect.*—Average angle of 50°.

*Internode length.*—An average of 4 mm.

Foliage description:

*Leaf shape.*—Oblanceolate.

*Leaf division.*—Simple.

*Leaf base.*—Acute.

*Leaf apex.*—Bluntly acute.

*Leaf fragrance.*—None.

*Leaf venation.*—Pinnate, upper vein color; 147B, lower vein color 144A.

*Leaf margins.*—Basal portion entire, crenate towards apex (upper $1/4^{th}$).

*Leaf arrangement.*—Alternate.

*Leaf aspect.*—Primarily flat (very slightly convexed).

*Leaf attachment.*—Petiolate.

*Leaf surface.*—Both surfaces smooth and glabrous.

*Leaf size.*—An average of 1.9 cm in length, 9.5 mm in width.

*Leaf quantity.*—34 per lateral branch.

*Leaf internode length.*—Average of 2 mm.

*Leaf color.*—Young leaves upper surface; 141A, young leaves lower surface; 143B, mature leaves upper surface; color between 147A and N189A, mature leaves lower surface; 138A.

*Petioles.*—Average of 3 mm in length and 0.6 mm in diameter, surfaces are smooth and glossy, strong, upper and lower surfaces are 144B in color.

Inflorescence description:

*Blooming period.*—About ten days in early to mid May in The Netherlands.

*Inflorescence type.*—Axillary cyme.

*Inflorescence size.*—Average of 1.1 cm in height and diameter.

*Flower number.*—Average of 7 flowers per inflorescence and 2,000 flowers per plant.

*Flower fragrance.*—None.

*Flower longevity.*—Average of 10 days, self-cleaning.

*Flower type.*—Single.

*Flower aspect.*—Rotate and slightly cup-shaped.

*Flower size.*—An average of 4 mm in diameter and 2 mm in depth.

*Peduncles.*—An average of 5 mm in length and 0.4 mm in diameter, 143C in color, smooth and glabrous, strength is moderately strong.

*Pedicels.*—An average of 3 mm in length and 0.3 mm in diameter, 143C in color, smooth and glabrous surface, strength is moderately strong.

*Flower buds.*—Globular in shape, an average of 1.2 mm in diameter and length, smooth, glabrous and slightly glossy surface, 144C in color becoming 144D at the apex.

*Sepals.*—4, occasionally 5 per flower, rotate arrangement, broadly deltoid in shape, entire margin, color on upper and lowers surface 144C, an average of 0.75 mm in length and 1 mm in width, broad acute apex, broadly cuneate base, upper and lower surface smooth and glabrous.

*Petals.*—4, occasionally 5 per flower, reniform in shape, glabrous and slightly velvety on upper and lower surface, entire margins, fused base, rounded apex, an average of 7.5 mm in length, 1 mm in width, color when opening and fully open upper and lower surface; 155C.

Reproductive organs:

*Pistils.*—Not formed, male flowers only.

*Stamens.*—4 per flower, filaments; average of 1 mm in length and N155A in color, anthers; average of 0.4 mm in length and 0.2 mm in width, oblong in shape, 158C in color, pollen; moderate in quantity, 155A in color.

*Fruit.*—Not formed, male flowers only.

It is claimed:

1. A new and distinct cultivar of Japanese holly plant named 'Annys5' as herein illustrated and described.

* * * * *